United States Patent [19]

Revel et al.

[11] Patent Number: 5,643,749
[45] Date of Patent: Jul. 1, 1997

[54] SOLUBLE INTERFERON α-RECEPTOR, ITS PREPARATION AND USE

[75] Inventors: Michel Revel, Rehovot; Carolina Abramovich, Yavne; Edward Ratovitski, Gan Yavne, all of Israel

[73] Assignee: Yeda Research and Development Co, Ltd., Rehovot, Israel

[21] Appl. No.: 328,256

[22] Filed: Oct. 24, 1994

[30] Foreign Application Priority Data

Oct. 24, 1993 [IL] Israel .................................. 107378

[51] Int. Cl.$^6$ .................................................. C12N 15/63
[52] U.S. Cl. ...................... 435/69.1; 536/23.5; 435/320.1
[58] Field of Search ........................... 435/69.1, 320.1, 435/240.2, 252.3; 536/23.5

[56] References Cited

FOREIGN PATENT DOCUMENTS 9218626  10/1992  WIPO .

OTHER PUBLICATIONS

Novick et al. 1992 FEBS Lett. 314, 445–448.

*Primary Examiner*—Stephen Walsh
*Assistant Examiner*—Karen E. Brown
*Attorney, Agent, or Firm*—Browdy and Neimark

[57] ABSTRACT

New forms of interferon α-receptors are provided. They may be prepared recombinantly and may be used in diagnosis and therapy.

12 Claims, 10 Drawing Sheets

EC = extracellular domain
IC = intracytoplasmatic domain
TM = transmembrane region
S = soluble domain
EC',"= end-deleted EC domains

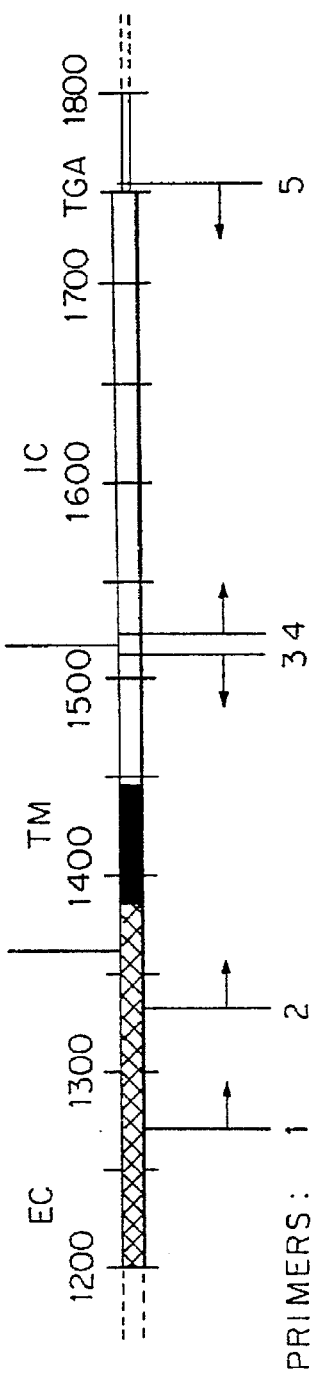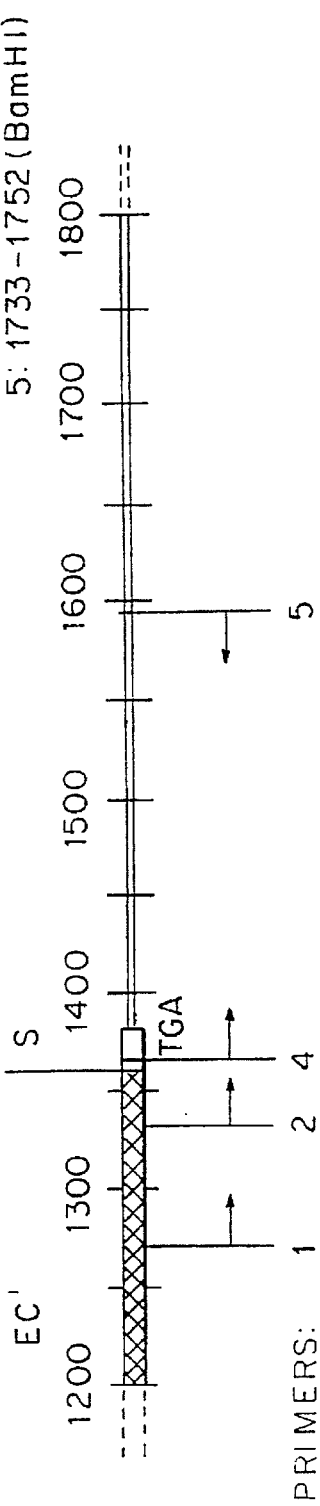
FIG. 2

FIG. 4

ALTERNATIVELY SPLICED IFN α-RECEPTOR FORM 1

NUCLEOTIDE SEQUENCE OF PCR CLONED FRAGMENT

```
                          1350                                    1380
   acgtgaattc  primer 1331-1342                        exon IX | exon X
CTG AAT AAA AGC AGT GTT TTT AGT GAC GCT GTA TGT GAG AAA ACA AAA CCA GGA AAT ACC

GC AGT GTT TTT AGT GAC GCT GTA TGT GAG AA

Transmembrane region    1410                                    1440
TCT AAA ATT TGG CTT ATA GTT GGA ATT TGT ATT GCA TTA TTT GCT CTC CCG TTT GTC ATT 1470                                    1500
TAT GCT GCG AAA GTC TTC TTG AGA TGC ATC AAT TAT GTC TTC TTT CCA TCA CTT AAA CCT 1530                                    1560
pr. 1498-1515    exon X | exon XI         primer 1522-1542
TCT TCC AGT ATA GAT GAG TAT TTC TCT GAA CAG CCA TTG AAG AAT CTT CTG CTT TCA ACT

TAT TTC TCT GAA CAG CCA TTG AAG AAT CTT CTG CTT TCA ACT 1590                                    1620
                                                 primer 1601-1619
TCT GAG GAA CAA ATC GAA AAA TGT TTC ATA ATT GAA AAT ATA AGC ACA ATT GCT ACA GTA..

TCT GAG GAA CAA ATC GAA AAA TGT TTC ATA ATT GAA AAT ATA AGC ACA ATT GCT ACA GTA..
```

In each block: First line: transmembranal cDNA (numbered, primers are underlined, TM domain is overlined). Second line: spliced-deleted cDNA form 1

---

AMINOACID SEQUENCE OF SPLICED-DELETED IFN-α-RECEPTOR FORM 1
Transmembranal form

```
(extracellular)   exon IX   |      exon X        |  exon XI (intracytoplasmic)
   (#427)            431aa  | 5aa {21aa} 23aa    |  77aa
CYS GLU lys thr lys pro     |gly..{ TM }..asp glu|tyr phe ser glu gln pro leu lys..
TGT GAG AAa aca aaa cca g   |ga...{    }..gat gag|TAT TTC TCT GAA CAG CCA TTG AAG..
         |                                                |
       1361                                             1519
         |_____|
                     ||
           ...TGT GAG AAT ATT TCT CTG AAC AGC CAT TGA...
           ...CYS GLU ASN ILE SER LEU ASN SER HIS  *
                  #427
```

Spliced-deleted IFN α-receptor cDNA form 1

FIG. 6

ALTERNATIVELY SPLICED IFN α-RECEPTOR FORM 2
Sequence of PCR cloned fragment

```
                                1290                                              1320
    gctcgaatt   primer 1270-1290                              --NcoI--
AAT TTG AAA OCA CTG ACT GTA TAT TGT GTG AAA GCC AGA GCA CAC ACC ATG GAT GAA AAG CCA CTG ACT GTA TAT TGT GTG AAA GCC AGA GCA CAC ACC ATG GAT GAA
            PRO LEU THR VAL TYR CYS VAL LYS ALA ARG ALA HIS THR MET ASP GLU 1350                                              1380
    acgtgaattc  primer 1331-1342                              exon IX | exon X
CTG AAT AAA AGC AGT GTT TTT AGT GAC GCT GTA TGT GAG AAA ACA AAA CCA GGA AAT ACC

AGT GAC GCT GTA TGT GAG
                            SER ASP ALA VAL CYS GLU

Transmembrane region        1410                                              1440
TCT AAA ATT TGG CTT ATA GTT GGA ATT TGT ATT GCA TTA TTT GCT CTC CCG TTT GTC ATT 1470                                              1500
TAT GCT GCG AAA GTC TTC TTG AGA TGC ATC AAT TAT GTC TTC TTT CCA TCA CTT AAA CCT 1530                                              1560
pr. 1498-1515   exon X | exon XI       primer 1522-1542
TCT TCC AGT ATA GAT GAG TAT TTC TCT GAA CAG CCA TTG AAG AAT CTT CTG CTT TCA ACT TAT TTC TCT GAA CAG CCA TTG AAG AAT CTT CTG CTT TCA ACT
            TYR PHE SER GLU GLN PRO LEU LYS ASN LEU LEU LEU SER THR 1590                                              1620
                                                primer 1601-1619
TCT GAG GAA CAA ATC GAA AAA TGT TTC ATA ATT GAA AAT ATA AGC ACA ATT GCT ACA GTA..

TCT GAG GAA CAA ATC GAA AAA TGT TTC ATA ATT GAA AAT ATA AGC ACA ATT GCT ACA GTA..
SER GLU GLU GLN ILE GLU LYS CYS PHE ILE ILE GLU ASN ILE SER THR ILE ALA THR VAL..
```

In each block:
First line: transmembranal cDNA (numbered, primers are underlined
            TM domain is overlined)
Second line: spliced-deleted cDNA form 2
Third line: aminoacid sequence of form 2

FIG. 7

Transmembranal IFN α-Receptor form

| | |
|---|---|
| MMVVLLGATTLVLVAVGPWVLSAAAGGKNLKSPQKVEVDIIDDNFILRWNRSDESVGNVT | 60 |
| FSFDYQKTGMDNWIKLSGCQNITSTKCNFSSLKLNVYEEIKLRIRAEKENTSSWYEVDSF | 120 |
| TPFRKAQIGPPEVHLEAEDKAIVIHISPGTKDSVMWALDGLSFTYSLLIWKNSSGVEERI | 180 |
| ENIYSRHKIYKLSPETTYCLKVKAALLTSWKIGVYSPVHCIKTTVENELPPPENIEVSVQ | 240 |
| NQNYVLKWDYTYANMTFQVQWLHAFLKRNPGNHLYKWKQIPDCENVKTTQCVFPQNVFQK | 300 |
| GIYLLRVQASDGNNTSFWSEEIKFDTEIQAFLLPPVFNIRSLSDSFHIYIGAPKQSGNTP | 360 |
| VIQDYPLIYEIIFWENTSNAERKIIEKKTDVTVPNLKPLTVYCVKARAHTMDEKLNKSSV | 420 |
| FSDAVCEKTKPGNTSKIWLIVGICIALFALPFVIYAAKVFLRCINYVFFPSLKPSSSIDE | 480 |
| YFSEQPLKNLLLSTSEEQIEKCFIIENISTIATVEETNQTDEDHKKYSSQTSQDSGNYSN | 540 |
| EDESESKTSEELQQDFV | 557 |

Splice deleted IFN α-Receptor form 1 (truncated)

| | |
|---|---|
| MMVVLLGATTLVLVAVGPWVLSAAAGGKNLKSPQKVEVDIIDDNFILRWNRSDESVGNVT | 60 |
| FSFDYQKTGMDNWIKLSGCQNITSTKCNFSSLKLNVYEEIKLRIRAEKENTSSWYEVDSF | 120 |
| TPFRKAQIGPPEVHLEAEDKAIVIHISPGTKDSVMWALDGLSFTYSLLIWKNSSGVEERI | 180 |
| ENIYSRHKIYKLSPETTYCLKVKAALLTSWKIGVYSPVHCIKTTVENELPPPENIEVSVQ | 240 |
| NQNYVLKWDYTYANMTFQVQWLHAFLKRNPGNHLYKWKQIPDCENVKTTQCVFPQNVFQK | 300 |
| GIYLLRVQASDGNNTSFWSEEIKFDTEIQAFLLPPVFNIRSLSDSFHIYIGAPKQSGNTP | 360 |
| VIQDYPLIYEIIFWENTSNAERKIIEKKTDVTVPNLKPLTVYCVKARAHTMDEKLNKSSV | 420 |
| FSDAVCENISLNSH | 434 |

Splice deleted IFN α-Receptor form 2 (with IC domain)

| | |
|---|---|
| MMVVLLGATTLVLVAVGPWVLSAAAGGKNLKSPQKVEVDIIDDNFILRWNRSDESVGNVT | 60 |
| FSFDYQKTGMDNWIKLSGCQNITSTKCNFSSLKLNVYEEIKLRIRAEKENTSSWYEVDSF | 120 |
| TPFRKAQIGPPEVHLEAEDKAIVIHISPGTKDSVMWALDGLSFTYSLLIWKNSSGVEERI | 180 |
| ENIYSRHKIYKLSPETTYCLKVKAALLTSWKIGVYSPVHCIKTTVENELPPPENIEVSVQ | 240 |
| NQNYVLKWDYTYANMTFQVQWLHAFLKRNPGNHLYKWKQIPDCENVKTTQCVFPQNVFQK | 300 |
| GIYLLRVQASDGNNTSFWSEEIKFDTEIQAFLLPPVFNIRSLSDSFHIYIGAPKQSGNTP | 360 |
| VIQDYPLIYEIIFWENTSNAERKIIEKKTDVTVPNLKPLTVYCVKARAHTMDESDAVCEY | 420 |
| FSEQPLKNLLLSTSEEQIEKCFIIENISTIATVEETNQTDEDHKKYSSQTSQDSGNYSNE | 480 |
| DESESKTSEELQQDFV | 496 |

SOLUBLE INTERFERON α-RECEPTOR, ITS PREPARATION AND USE

FIELD OF THE INVENTION

The present invention relates to new forms of interferon α-receptors (IFN α-receptors), their preparation, compositions containing them, and uses thereof in diagnosis and therapy.

BACKGROUND OF THE INVENTION

Interferons belong to the family of cytokines which are cell-secreted proteins that typically act on target cells via specific plasma membrane receptors present on the surface of the target cells. A common feature of these receptors is the presence of an internal sequence of hydrophobic amino acids forming the transmembranal(TM) domain, which anchors the receptor in the outer membrane of the cell (Bazan, J. F., Proc. Natl. Acad. Sci. USA 87 6934–6938 (1990)). A human type I IFN receptor, designated IFN α-receptor protein (IFNAR) was characterized by cloning of its cDNA (Uze, G., and Gresser, I., Cell 60, 225–234 (1990)). This cDNA encodes an IFNAR protein having a 21 amino acid-long hydrophobic transmembranal region, which separates an N-terminal extracellular (EC) domain of 436 amino acids, from a C-terminal intracellular (IC) domain of 100 amino acids (see FIG. 1, scheme 1). It has been shown that the EC domain is involved in ligand binding (Benoit, P., et al., J. Immunol. 150, 707–716 (1993); Novick, D., et al., FEBS letters 314, 445–448 (1992)).

The existence of soluble non-membrane bound forms of receptors has been recognized (Fernandez-Botran, R., FASEB Journal 5, 2567–2574 (1991)). Such receptors are often formed by a proteolytic cleavage which occurs between the extracellular domain and the transmembranal region, thereby resulting in the shedding of a truncated receptor (Nophar, Y., et al., EMBO J.9, 3269–3278 (1990); Mullberg, J., et al., Eur. J. Immunol. 23, 473–480 (1993). Moreover, cells have also been found to synthesize other forms of cytokine receptors lacking the transmembranal and intracellular domains, which are, however, not as a result of proteolytic cleavage, but due to a differential processing of the receptor gene transcripts (Raines, M. A. et al., Proc. Natl. Acad. Sci. USA, 88, 8203–8207 (1991); Lust, J. A. et al., Cytokine 4, 96–100 (1992)). These non-transmembranal or "soluble" forms are characterized by a novel amino acid sequence at the C-terminus, making them distinct proteins, with probably distinct functions. Heretofore, non-transmembranal or "soluble" IFN α-receptors have not been described.

SUMMARY OF THE INVENTION

It has now been surprisingly and unexpectedly found, in accordance with the present invention, that non-membranal forms of the IFN α-receptor, produced by differential processing of the receptor gene transcripts, exist in cells.

The present invention thus provides new IFN α-receptor proteins which have an amino acid sequence different from the IFN α-receptor cloned by Uze (supra). These receptors are recognized by monoclonal antibodies specific for the IFN α-receptor in non-membranal compartments of the cell. These soluble IFN receptors are likely to regulate the response of human cells to IFNs, either by competing with the cell membrane receptor for ligand binding, or else by carrying IFN-mediated functions within the cell.

More specifically, the present invention provides an isolated DNA sequence encoding a mammalian, soluble, non-membrane bound form of an interferon α-receptor (IFNAR).

The above IFNAR DNA sequence of the invention encodes a polypeptide product of prokaryotic or eukaryotic host expression having all or part of the primary structural confirmation and the biological activity of mammalian soluble, non-membrane bound form of an IFNAR.

The DNA sequence of the invention may be any one of the following:

a) cDNA clones having a nucleotide sequence derived from the coding region of a native mammalian IFNAR gene;

b) DNA sequences capable of hybridization to clones of (a) under moderately stringent conditions and which encode biologically active, soluble, non-membrane bound IFNAR;

c) DNA sequences which are degenerate, as a result of the genetic code, to the DNA sequences defined in (a) and (b) and which encode biologically active, soluble non-membrane bound IFNAR.

The above DNA sequence of the invention may encode all or part of the IFNAR form 1 or form 2, the sequences of which are depicted in FIG. 7, which forms are described herein below in greater detail.

The present invention also provides a recombinant expression vector comprising the above DNA sequence of the invention, and a process for preparing a mammalian, soluble, non-membrane bound form of an IFNAR or an analog thereof, comprising culturing a suitable host cell comprising the above vector under suitable conditions promoting expression.

The present invention further provides a mammalian, soluble, non-membrane bound form of an IFNAR, or a mutein, fused protein, salt, functional derivative or active fraction thereof.

The above soluble form of an IFNAR of the invention may be of human origin, may be the splice-deleted form 1 or form 2 of IFNAR having a molecular weight of about 55 kd or about 95 kd, respectively, and which may have, respectively, all or part of the sequence of amino acid residues greater than about 80% similar to the sequence of amino acids 1–434 or 1–496 depicted in FIG. 7.

The present invention further provides a composition containing, as active ingredient, any of the above IFNAR forms and a suitable diluent carrier and/or excipient. The composition may be used for inhibition, modulating or modifying the activities of IFN-α and IFN-β subtypes in cells or tissues. The composition may also be used for qualitative and/or quantitative diagnostic determination of the kinds of IFN-α or IFN-β subtypes in vivo or in vitro.

Moreover, the present invention also provides a pharmaceutical composition formulated from the above composition of the invention and a pharmaceutically acceptable diluent, carrier and/or excipient; the pharmaceutical composition being for the modulation, inhibition or modification of the activities of IFN-α and IFN-β subtypes in cells and/or tissues; or for the treatment of patients having excess amounts of IFNs as a result of IFN treatment or excess endogenous IFN production.

The above aspects of the present invention and others will become apparent from the following detailed description of the invention and the accompanying figures.

The positions of the new junctions created by the deletions are indicated, as well as the position of the termination codons.

FIG. 2: shows a schematic representation of the soluble IFNAR cDNA form with the novel soluble (S) domain (lower part) in comparison to the known transmembranal IFNAR cDNA (upper part), as is described in Examples 1 and 2. Positions of the primers used for PCR reactions are indicated, as well as deletions and new junctions.

Figure 3:
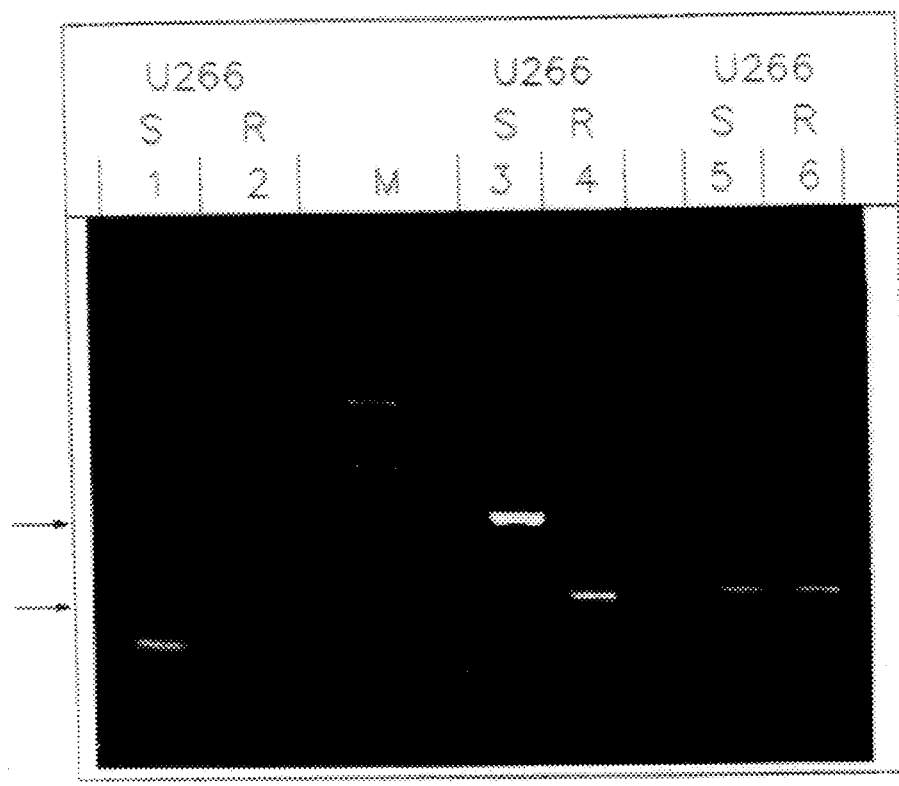

FIG. 3: shows a reproduction of an agarose gel electrophoresis, ethidium bromide stained, analysing the size of the PCR products from $U266^R$ and $U266^S$ cells, as is described in Examples 1 and 2.

Lanes 1,2: Reaction A with primers 2+3 of FIG. 2.

Lanes 3,4: Reaction B with primers 2+5 of FIG. 2 (products shown by arrows)

Lanes 5,6: Reaction C with primers 4+5 of FIG. 2.

FIG. 4: illustrates a portion of the nucleotide sequence of the IFNAR cDNA form with the novel S domain (second line of each numbered block SEQ ID NO: 3), compared to the known transmembranal cDNA (first line of each numbered block residues 61-360 of SEQ ID NO: 1) with the numbering according to transmembranal cDNA, as is described in Example 2. The position of primers is underlined, and the transmembranal domain is overlined. Primer 1331-1342, with EcoRI restriction site tail (shown in lower case letters), corresponds to SEQ ID NO: 2. Lower part: Amino acid sequence of novel IFNAR cDNA form 1 (SEQ ID NO: 6), showing a frameshift creating 7 C-terminal residues unique to the cDNA form 1. The nucleotide sequence shown for the spliced-deleted IFN α-receptor cDNA form 1 is residues 24-53 of SEQ ID NO: 3. Exon boundaries are indicated as previously reported (Lutfalla, G., et al., J. Biol. Chem. 267, 2802-2809 (1992)). Partial amino acid sequences of exon junctions of the transmembranal form correspond to SEQ ID NO: 4 and 5, with the corresponding nucleotide sequences being residues 94-114 and 253-282 of SEQ ID NO: 1, respectively.

Figure 5:
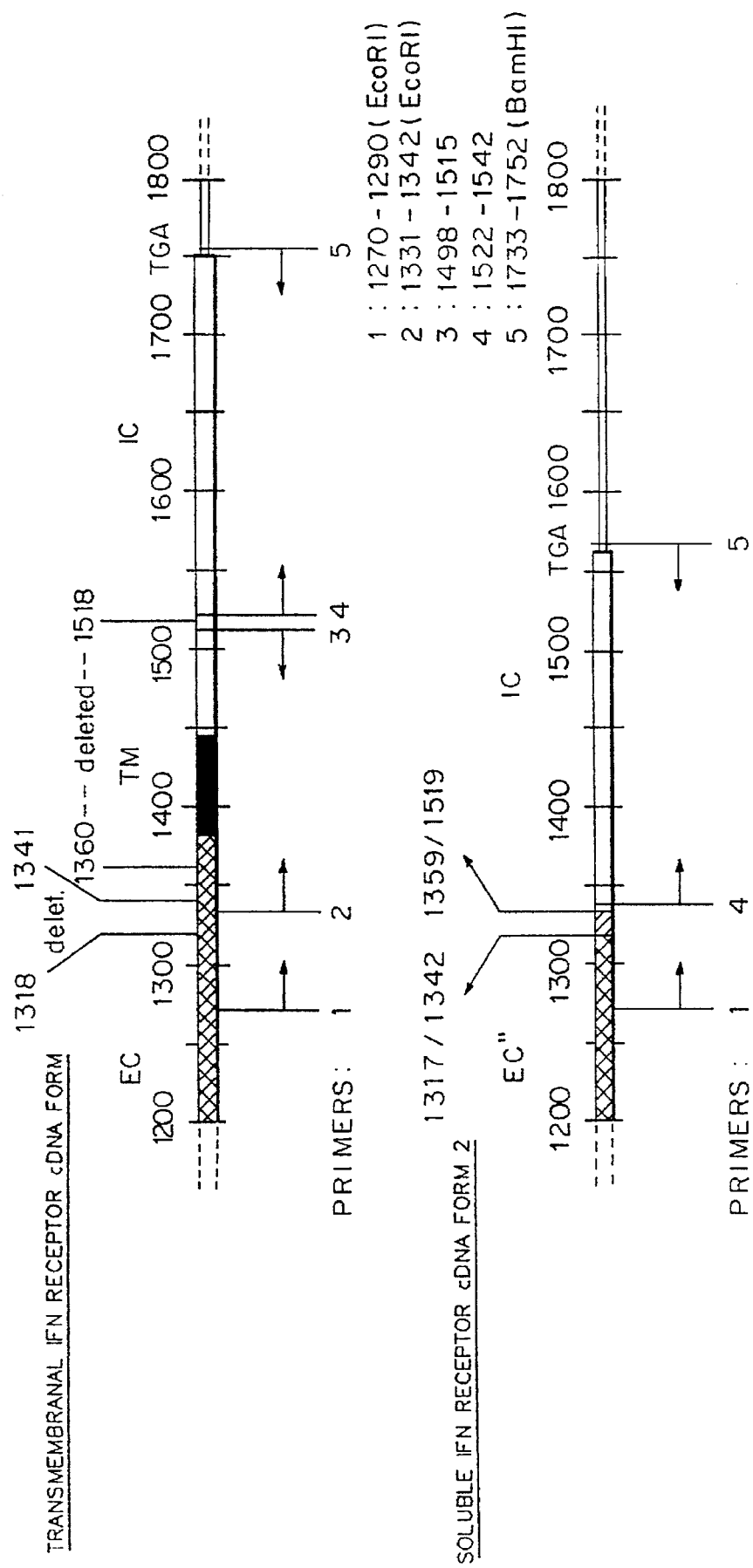

FIG. 5: shows a schematic representation of the soluble IFNAR cDNA form with the shortened IC' domain (lower part) in comparison to the known transmembranal IFNAR cDNA (upper part, as is described in Example 3. Positions of the primers used for PCR reactions are indicated, as well as deletions and new junctions.

FIG. 6: illustrates a portion of the nucleotide sequence from the IFNAR cDNA form with the shortened IC' domain according to the present invention (second line of each numbered block), compared to the known transmembranal cDNA (first line of each numbered block; SEQ ID NO: 1), as described in Example 3. The amino acid sequence of the IFNAR with the shortened IC' domain (SEQ ID NO: 9) is shown in the third line; gaps indicate deleted sequences. Numbering according to transmembranal cDNA. The position of primers is underlined and the transmembranal domain is overlined. Primer 1331-1342 and primer 1270-1290, each with their EcoRI tails (shown in lower case letters) correspond to SEQ ID NO: 2 and SEQ ID NO: 7, respectively. Exon boundaries are indicated as in FIG. 4.

FIG. 7: shows the amino acid sequences, as described in Example 3, of the spliced-deleted soluble IFNAR form 1 (SEQ ID NO: 11) with the novel S domain underlined as well as the double-deleted form 2 (SEQ ID NO: 12) with the shortened IC' domain and with the underlined 6-amino acid long extracellular region containing a cysteine, which is retained between the two deletions. The known transmembranal IFNAR (SEQ ID NO: 10) is shown in comparison with its transmembranal domain underlined.

Figure 8:
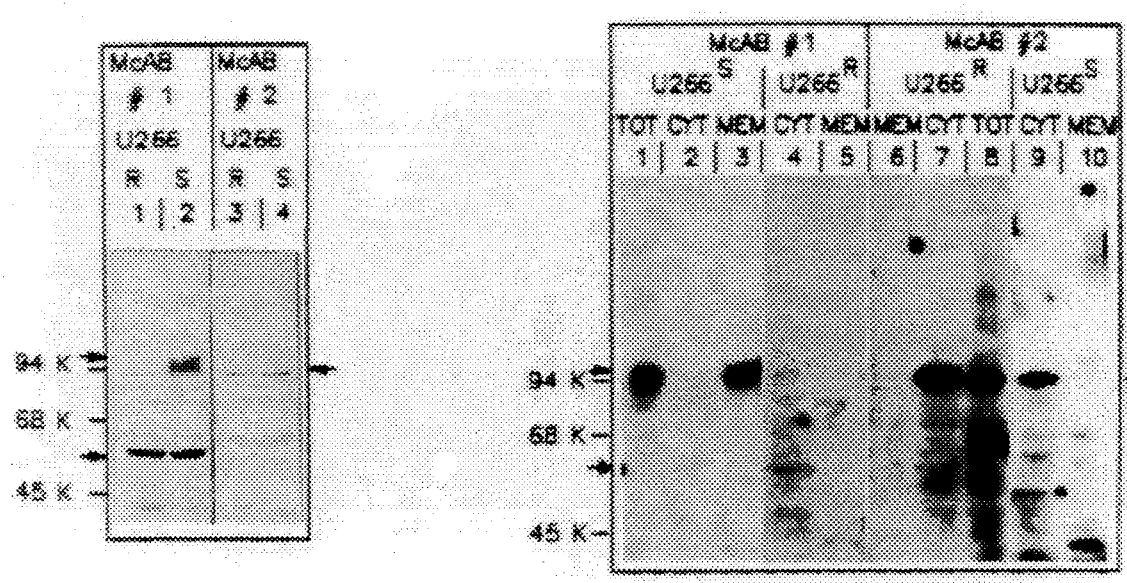

FIG. 8: shows a reproduction of Western immunoblots of proteins from $U266^S$ and $U266^R$ cells reacted with mAb#1 and mAb#2, as described in Example 4. Left panel: Total CHAPS extract. Left arrows show the 110 Kd transmembrane IFNAR and the 55 Kd protein. Right arrow shows the 95 Kd protein.

Right panel: Total CHAPS extract (TOT), soluble cytoplasmic compartment (CYT) and cell membranes (MEM). Left arrow shows the 110 Kd transmembrane IFNAR. Right arrow shows the 95 Kd cytosolic protein.

Figures 9A, 9B:
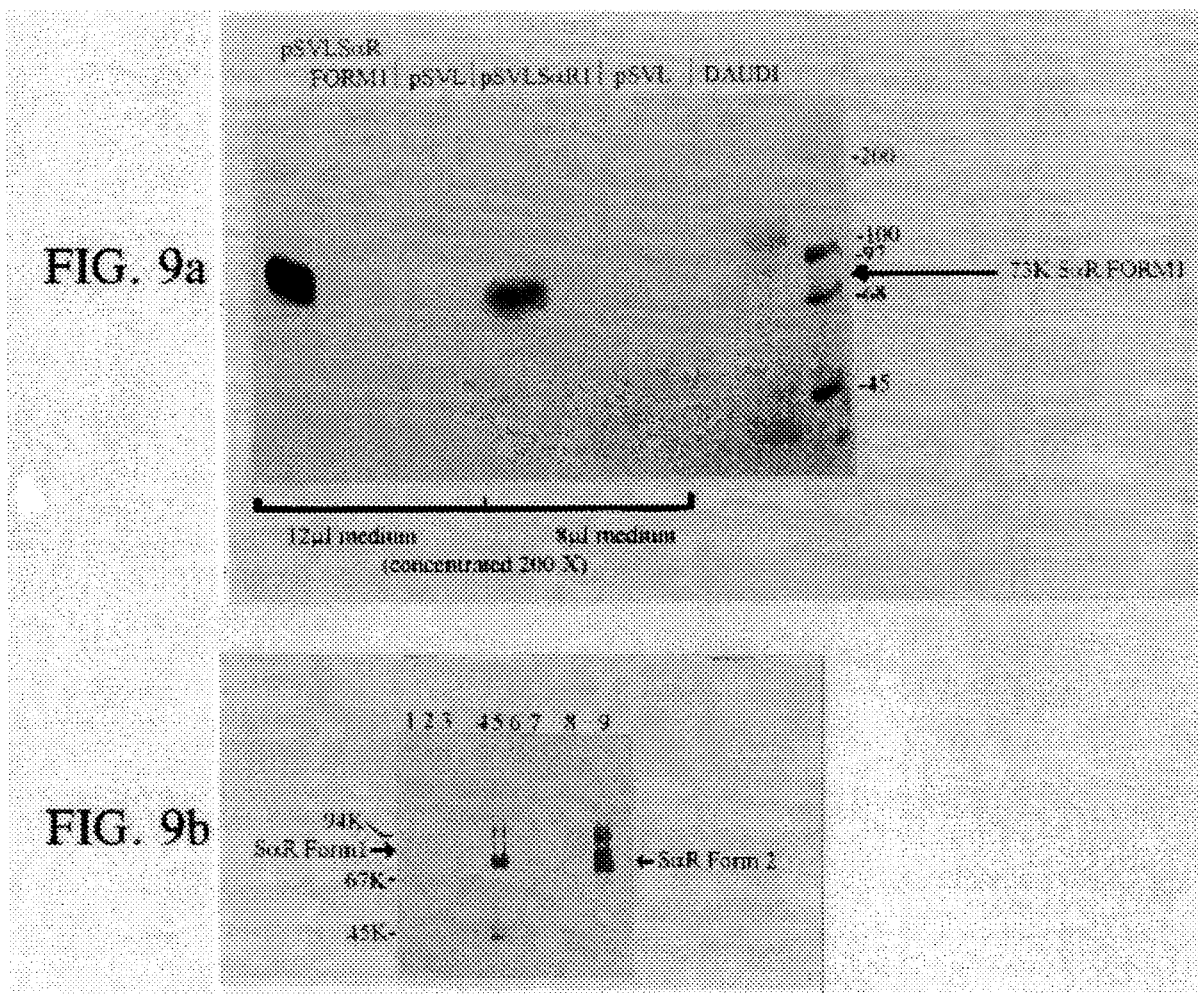

FIG. 9 (a and b): shows reproductions of Western blots of recombinantly produced soluble IFNAR proteins secreted from transfected COS-7 cells (FIG. 9a) and recombinantly produced soluble IFNARs secreted from transfected COS-7 cells as well as associated with cell membranes, intracellular compartments (cytosol) and cell nuclei (FIG. 9b), as described in Example 5(a).

Figure 10:
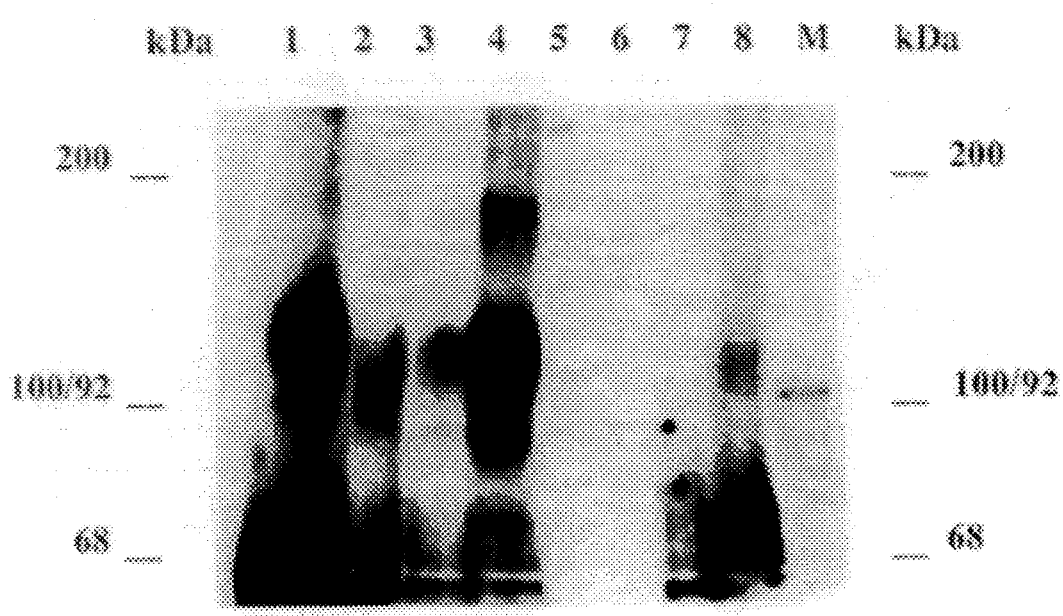

FIG. 10: shows a reproduction of an SDS-PAGE gel on which was separated immunoprecipitated products of the cross-linkage between recombinantly produced soluble Form 1 IFNAR and radiolabelled IFN, demonstrating the IFN-binding activity of recombinant soluble Form 1 IFNAR, as described in Example 5(a).

DETAILED DESCRIPTION OF THE INVENTION

The present invention is concerned with new forms of the human IFN α-receptor mRNAs and proteins, characterized by their synthesis in human cells through alternative splicing mechanisms. The sequence established for two new forms of IFN α-receptor cDNAs indicate that the corresponding mRNAs encode novel polypeptide sequences defining proteins which lack the transmembranal region. Such non-membranal IFNAR forms are demonstrated in the soluble cytoplasmic compartment of human cells. The proteins may also be secreted from the cell into the extracellular space, but are distinguished from other soluble receptor forms, which are derived from membrane bound receptors by proteolytic cleavage which released the extracellular domain of these receptors.

Figure 1:
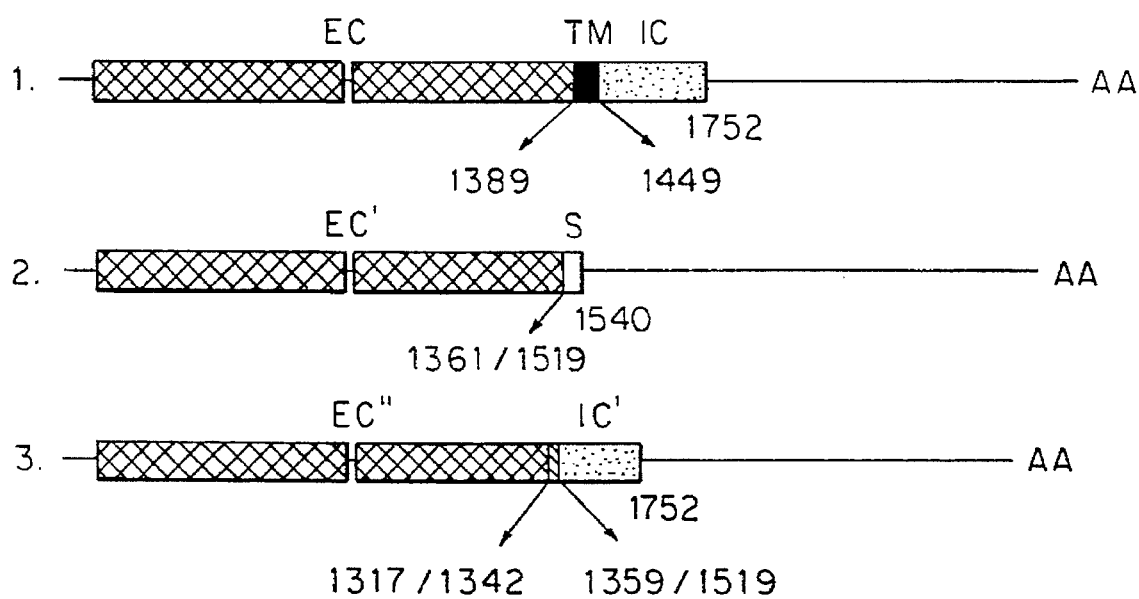
FIG. 1: shows a schematic representation, as is described in Example 1, of the cDNAs for 1) the known transmembranal IFNAR form, 2) the truncated IFNAR form with the novel S domain, according to the present invention, 3) the double deleted IFNAR form with shortened IC' domain, according to the present invention.

The potential functions of soluble receptors as regulators of cytokine activities have been described (Fernandez-Botran, 1991). The existence of a mechanism by which cells produce mRNAs encoding two non-membrane bound or soluble forms of IFN α-receptor, suggests that the two forms each have some function for the cell. These forms would not anchor in the membrane, and may be secreted outside the cells or be found in the cytosol (soluble cell compartment). The one form containing the ligand binding, extracellular domain (EC) followed directly by the intra-cytoplasmic domain without the TM domain (FIG. 1, scheme 3), should still be able to function in transduction of signals such as those generated by cytokine binding, for example, within the interior of the cell. The other form in which the EC domain is followed by the S-domain (FIG. 1, scheme 2), but lacks both the transmembrane and intra-cytoplasmic domains, would not function in signal transduction. The EC domain of the IFNAR (residues 22-427) is known to contain IFN binding activity (Benoit, P. et al., 1993; Novick D., et al 1992 see above). Therefore, the soluble IFNAR forms encoded in the cell mRNA according to the present invention, could either bind IFN and compete with IFN activity on the cell surface, acting as IFN antagonists, or regulate in other ways the activities of the multiple IFN subtypes. Being synthesized within the cell, these proteins can also interact with other cellular proteins involved in the biological response to IFNs. This would not be the case for soluble IFN α-receptors produced by proteolytic cleavage outside the cell plasma membrane of normally membrane bound receptors.

Applications of the novel, soluble IFNAR forms of the present invention could be for inhibiting, modulating or modifying the activities of IFN-α and IFN-β subtypes in cells, tissues and organisms. IFNs have antiviral, antiproliferative and immunoregulatory functions (Baron, S. et al.(eds), Interferon: Principles and Medical Applications, The University of Texas Medical Branch at Galveston, (1992)). IFNs are used clinically to treat viral diseases (e.g. papillomatoses, hepatitis, etc.) malignancies (e.g. leukemias, hormone-dependent cancers, etc.) and immunological dysfunctions (e.g. multiple sclerosis). These beneficial effects of IFNs may be naturally modulated by the different forms of the IFN m-receptor such as those of the present invention. On the other hand, excess of IFN may be detrimental and has been implicated in some auto-immune diseases, in graft rejections and hematopoietic deficiencies (locus cited). These conditions may benefit from inhibitors of IFN action. Furthermore, cells can differ in their response to IFN-α and IFN-β subtypes (Rosenblum, M. G. et al., J. Interferon Res. 10,141–151 (1990)), and the cell response to IFN subtypes may be modulated by some of the cell-synthesized soluble IFNAR forms. The isolation and identification of novel IFNAR cDNAs according to the present invention, will allow the production of the natural cell-synthesized soluble IFN α-receptor forms by recombinant DNA technology and the study of their functions by overexpression in transfected cells, or by addition to cell cultures.

The soluble IFNAR forms according to the present invention may be used to prepare pharmaceutical compositions for inhibiting, modulating or modifying the activities of IFN-α and IFN-β subtypes. Such pharmaceutical compositions may be used, for example, for the treatment of various disorders, as noted above, in which patients have an excess of IFNs as a result of receiving large doses of IFN in therapy or as a result of abnormally high endogenous production of IFNs. The pharmaceutical compositions may be prepared by any of the well known procedures in which the active ingredient, soluble IFNAR, is admixed with pharmaceutically acceptable diluents, carriers or excipients. Actual dosages and modes of administration of such pharmaceutical compositions will be determined by the professional practitioners.

The soluble IFNARs of the present invention may also be used to prepare compositions for diagnostic purposes, for example, for the qualitative and/or quantitative determination of the kinds of IFN-α and IFN-β subtypes in in vivo or in in vitro diagnostic assays. In these compositions, the soluble IFNARs may be labelled by any of the established labelling procedures, for examples, radio-labelling, fluorescent labelling, enzyme-linkage, antibody-linkage, etc. Preparation of the above compositions and application of the above compositions in diagnostic assays will be by any of the well-established procedures.

The soluble IFNARs of the present invention may also be applied in affinity chromatographic methods for the purification of IFN-α and IFN-β subtypes. In such applications, the soluble IFNARs may be attached to any of the known affinity chromatographic support matrices, using any of the standard methods therefor, for example, chemical cross-linking.

As used herein, the term "muteins" refers to analogs of the soluble IFNAR proteins in which one or more of the amino acid residues of the natural soluble IFNAR are replaced by different amino acid residues or are deleted, or one or more amino acid residues are added to the natural sequence of the soluble IFNAR, without changing considerably the activity of the resulting product. These muteins are prepared by known synthesis and/or by site-directed mutagenesis techniques, or any other known technique suitable therefor.

The term "fused protein" refers to a polypeptide comprising a soluble IFNAR according to the invention, or a mutein thereof fused with another protein which has an extended residence time in body fluids. The soluble IFNAR may thus be fused to another protein, polypeptide or the like, e.g. an immunoglobulin or a fragment thereof.

The term "salts" herein refers to both salts of carboxyl groups and to acid addition salts of amino groups of a soluble IFNAR protein, muteins and fused proteins thereof. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids such as, for example, hydrochloric acid or sulfuric acid, and salts with organic acids such as, for example, acetic acid or oxalic acid.

"Functional derivatives" as used herein cover derivatives of a soluble IFNAR and its fused proteins and muteins, which may be prepared from the functional groups which occur as side chains on the residues or the N- or C-terminal groups, by means known in the art, and are included in the invention as long as they remain pharmaceutically acceptable, i.e. they do not destroy the activity of the protein and do not confer toxic properties on compositions containing it. These derivatives may, for example, include polyethylene glycol side-chains which may mask antigenic sites and extend the residence of a soluble IFNAR in body fluids. Other derivatives include aliphatic esters of the carboxyl groups, amides of the carboxyl groups by reaction with ammonia or with primary or secondary amines, N-acyl derivatives of free amino groups of the amino acid residues formed with acyl moieties (e.g. alkanoyl or carbocyclic aroyl groups) or O-acyl derivatives of free hydroxyl groups (for example that of seryl or threonyl residues) formed with acyl moieties.

As "active fractions" of the soluble IFNAR, its fused proteins and its muteins, the present invention covers any fragment or precursors of the polypeptide chain of the protein molecule alone or together with associated molecules or residues linked thereto, e.g. sugar or phosphate residues, or aggregates of the protein molecule or the sugar residues by themselves, provided said fraction has the same biological activity and/or pharmaceutical activity.

The invention will now be illustrated by the following non-limiting examples. It should be noted that, unless otherwise indicated, the methods described in the examples are standard, well established methods, widely used in genetic engineering. Accordingly, reference will be made to and is thereby incorporated herein, various publications in which the methods are fully detailed. Further, where details are provided concerning manufacturers, it is to be understood that the associated methods are according to the manufacturer's protocols.

EXAMPLE 1

Multiple IFN α-receptor gene transcripts

Human myeloma cells U266$^S$ are sensitive to IFN-α and IFN-β subtypes for growth-inhibition and for induction of (2'-5') A synthetase. The U266$^S$ cells were compared to U266$^R$ variants, which have lost growth-inhibition by the above IFNs. Total RNA was prepared by the guanidine thyocyanate method (Chirgwin J. J. et al., Biochemistry 18, 5294–5300 (1979). From RNA of U266$^S$ and U266$^R$ cells, cDNA was produced by Reverse Transcriptase primed with an oligo-deoxyribonucleotide complementary to nucleotides 1729–1749 of the IFNAR cDNA (this primer is adjacent to the end of the coding frame of the transmembranal IFNAR cDNA, FIG. 1, scheme 1). The polymerase chain reaction (PCR) was then used to amplify DNA fragments of the above cDNA product, according to established procedures ((Ehrlich H. A., editor, PCR Technology, Stockton Press, New York, (1989)). Three pairs of sense/antisense primers were used, which correspond to the following nucleotides of the transmembranal IFNAR cDNA (see FIG. 2, upper part for numbering):

PCR reaction A: 1342–1361 / 1498–1515
PCR reaction B: 1331–1342 / 1733–1752
PCR reaction C: 1522–1542 / 1729–1749

In reaction B, the sense and antisense primers used had tails containing EcoRI and BamHI sites respectively; after digestion with these restriction enzymes, the products would be 10 bp longer than expected. The PCR products analyzed by electrophoresis on agarose gels followed by ethidium bromide staining, are shown in FIG. 3.

In reaction A, the expected 173 bp product was observed when using RNA from U266$^S$ cell (lane 1) whereas no product was observed when RNA from U266$^R$ cells was used (lane 2). This result indicated that the IFN receptor transcripts of U266$^R$ cells have some deletion in the region between nucleotides 1342 and 1515, which prevented one of the primers to initiate the PCR reaction.

In reaction B, the expected 420 bp size product (as defined by primers 2 and 5 of FIG. 2), was observed with U266$^S$ RNA. In addition, a new DNA band whose size is estimated at 260 bp was found (lane 3). With U266$^R$ RNA, the smaller product was observed, but the larger band was missing (lane 4). This result revealed the existence of transcripts with a deletion of approximately 160 bp in both U266$^S$ and U266$^R$ cells.

In reaction C, the same product was observed with both U266$^S$ and U266$^R$ RNA, indicating no modification of this region between primers 4 and 5 of FIG. 2. Examination of the position of the primers used in reaction A and B, indicated that the observed deletions affect the transmembranal region of the IFNAR cDNA (FIG. 2).

EXAMPLE 2

Spliced-deleted IFN α-receptor form 1

In order to determine the nucleotide sequence of the new forms of IFNAR cDNA, a PCR reaction similar to B in Example 1, was carried out with RNA from U266$^S$ cells. The primers used (primers 2 and 5 FIG. 2) had tails containing an EcoRI restriction site for primer 1331–1342, (shown in lower case in FIG. 4) and a BamHI site for primer 1733–1752. After the PCR reaction, the products were incubated with EcoRI and BamHI, and separated by agarose gel electrophoresis. The small 260 bp product was cut out from the gel and ligated into Bluescript vector KS$^+$ (Stratagene Cloning System, Lajolla, Calif.), which had been cut by EcoRI and BamHI. The ligated plasmids were transfected into competent E. coli cells, transfectant colonies were isolated and plasmid DNA prepared. The presence of the 260 bp was verified by cutting with EcoRI and BamHI.

Uncut plasmid DNA was sequenced by the dideoxynucleotide method from the T3 primer of the Bluescript vector (Stratagene Cloning Systems, LaJolla, Calif.). The complementary strand was sequenced from an antisense primer 1601–1619. FIG. 4 shows the sequence obtained for the small PCR product in comparison to the sequence of the transmembranal IFNAR cDNA. A deletion from nucleotide 1362 to 1518 (157 bp) was observed, completely removing the transmembranal region (see FIG. 2).

The PCR product obtained with U266$^R$ RNA (as in FIG. 3, lane 4), was similarly cloned in Bluescript vector and sequenced. The resulting plasmids yielded the same sequence as for the small PCR product of U266$^S$ cells.

The novel sequence obtained indicates that the entire exon X containing the transmembranal region is spliced out, and that the last 4 codons of exon IX are missing as well. This alternative splicing causes a frameshift after codon 427 (Glu) in the extracellular domain, and predicts a truncated protein with 7 amino acids Asn-Ile-Ser-Leu-Asn-Ser-His (amino acids 3–9 of SEQ ID NO: 6), not found in the previously known IFNAR protein (FIG. 4, lower part). This new form of the IFN-α receptor is designated as spliced-deleted form 1, and is characterized by a new domain S which follows the end-deleted EC domain (FIG. 2 lower part).

It was verified that the large PCR product obtained with U266$^S$ RNA (420 bp in FIG. 3, lane 3), contained the transmembranal region and the normal exon X/exon XI boundary of the transmembranal IFNAR cDNA, indicated in FIG. 4.

EXAMPLE 3

Spliced deleted IFN α-receptor form 2

Another form of IFNAR with a double deletion was discovered. This spliced-deleted form 2 was detected in PCR reactions carried out with a more upstream primer corresponding to nucleotides 1270–1290 of the IFNAR cDNA (primer 1 in FIG. 5). This sense primer with a 5' tail containing an EcoRI site was used in conjunction with the 1733–1752 antisense primer with a BamHI site (primer 5 in FIG. 5). The PCR products obtained with U266$^R$ RNA were digested with EcoRI and BamHI, electrophoresed on agarose gel and the DNA band observed at approximately 300 bp, was cut out from the gel. After cloning in Bluescript vector as in Example 2, the plasmid DNA was sequenced. The sequence obtained (FIG. 6) indicates again a deletion of the transmembranal region. As can be seen, in comparison to the transmembranal IFNAR cDNA, this spliced-deleted form 2 has two in-phase deletions of nucleotides 1318 to 1341 (24 bp) in exon IX and of nucleotides 1360 to 1518 (159 bp, i.e. the end of exon IX and all of exon X).

The structure of the spliced-deleted form 2 IFNAR cDNA is schematically shown in FIG. 5 (lower part). In the protein encoded by this novel IFNAR cDNA, the extracellular domain is missing 8 codons following residue 413 (Glu) of the transmembranal form, continues with 6 amino acids (residues 422–427 still in exon IX), and after a further deletion of 53 amino acids (including the transmembranal region) continues in the intracytoplasmatic domain from Tyr-481. The predicted IC domain is 77 amino acids long instead of 100 in the transmembranal form.

The amino acid sequence of this spliced-deleted form 2 of the IFN α-receptor is shown in FIG. 7 (bottom), as compared to the truncated form 1 and the transmembranal form. It is notable that in form 2, the 6 amino acids (underlined in FIG. 7) which are found between the two deletions contain a cysteine, thereby conserving the 8 cysteine residues found in the extracellular domain of the transmembranal form and the splice-deleted form 1.

The two new forms of the IFN-α receptor according to the present invention comprise 434 and 496 amino acids, respectively, while the transmembranal form (FIG. 7) comprises 557 amino acids. The two new forms are depicted in schemes 2 and 3 of FIG. 1.

EXAMPLE 4

Non-membranal IFN α-receptor proteins

The proteins encoded by the two new forms of IFNAR cDNA were examined in $U266^R$ cells, which do not contain RNA transcripts for the transmembranal form of IFNAR, but only the alternatively spliced-deleted forms. For this purpose, immunoblots were made with various monoclonal antibodies (mAbs) against the recombinant IFNAR protein. The results shown were obtained with two antibodies: mAb #1 or 64G12 (Benoit et al., 1993 see above); and mAb #2 or 21.4 (Novick et al., 1992 see above). Total proteins from U266 cells were extracted with buffers containing 10 mM CHAPS detergent (3-(3-Cholamido-propyl)-dimethyl-ammonio)-1-propane-sulfonate), subjected to electrophoresis in sodium dodecyl-sulfate polyacrylamide gels, blotted onto nitrocellulose, and reacted with mAbs followed by labelled goat anti-mouse immunoglobulin antibodies. To determine the intracellular localization of the protein, cells were lysed by hypotonic shock and the cytosol fraction of the cell (soluble cytoplasmic compartment) was compared to the membrane fraction, prepared as described (Chebath, J. et al., J. Biol. Chem. 262, 3852–3857 (1987)). For comparative purposes, $U266^S$ cells were also lysed and the cytosol and membrane fractions were isolated in the above-mentioned fashion.

Comparison of $U266^R$ and $U266^S$ cell protein extracts shows that the IFN α-receptor protein of about 110 Kd which is recognized by mAb #1 in $U266^S$ is completely absent in $U266^R$ (FIG. 8, left panel, lanes 1, 2). This protein is membranal (right panel, lane 3) as expected for the product of the transmembranal IFNAR mRNA product. In addition, mAb #1 recognized a protein of about 55 Kd: this protein is present in $U266^R$ cells (FIG. 8 left panel, lanes 1, 2) and, therefore, is likely to be the product of a spliced-deleted mRNA lacking the transmembranal region found in $U266^R$ cells. Indeed, the 55 Kd protein is not present in the membrane, but is detected only in the cytosol of both in $U266^S$ and $U266^R$ cells (FIG. 8, right panel, lanes 2–5).

In similar immunoblots, mAb #2 recognized another form of the IFN α-receptor which migrates approximately as a 95 Kd protein, and which is present in both $U266^S$ and $U266^R$ cells (FIG. 8, left panel, lanes 3, 4). The 95 Kd protein is clearly abundant in the cytosol and absent from membranes (FIG. 8, right panel, lanes 6–10). It was verified that when this protein of about 95 kd is first concentrated by immunoprecipitation by mAb #2, it is then recognized also by mAb #1 on immunoblots indicates that this cytosolic protein is a form of IFN α-receptor for which mAb #1 has lower affinity than mAb #2. That this 95 Kd protein is a product of spliced-deleted IFNAR mRNA is supported by the fact that it is present in both $U266^S$ and $U266^R$ cells, and that it is not membranal.

The fact that different forms of IFNAR protein can be recognized by mAb against recombinant IFNAR indicates, on the one hand, that the different forms are closely related, i.e. have sequence identity, and on the other, that there exists heterogeneity of the receptor proteins. The 95 Kd cytosolic form could be the product of the splice-deleted form 2 cDNA described in Example 3. This protein could function in the cytoplasm in the residual response to IFN of $U266^R$ cells. An early response of cells to IFN is the activation of transcription factors ISGF3 and IRF-1 which bind to the IFN responsive enhancers of a number of IFN-activated genes (Levy, D. E. et al., Genes Dev.3, 1362–1371 (1989); Harada, H., Cell 58, 729–739 (1989)). It was observed (Abramovich C., Ph.D. Thesis, Weizmann Institute of Science (1993)) that IFN activates IRF-1 in $U266^R$ cells, as well as in $U266^S$ cells. This response to IFN could be mediated by a spliced-deleted IFNAR cDNA product in $U266^R$ cells. In contrast, ISGF3 is induced only in $U266^S$ cells, indicating it requires the membranal IFNAR protein.

The 55 Kd protein may be the product of the truncated splice-deleted form 1 described in Example 2. This shorter truncated form, may be secreted from the cells and could act as a competitive inhibitor of IFN binding.

EXAMPLE 5

Recombinant production of soluble IFNAR proteins, fusion products, fragments and muteins thereof (a)Recombinant production of soluble IFNAR proteins, Form 1 and Form 2:

As is set forth in Examples 1–4 above, there exist two forms of differentially spliced mRNAs encoding new forms, Form 1 and Form 2, of the IFNAR protein which lack the transmembranal region. Using standard procedures of recombinant DNA technology (see, for example, Maniatis et al., Molecular Cloning: A Laboratory Manual, Cold Spring Harbor Laboratory, New York, 1982; Sambrook et al., Molecular Cloning: A Laboratory Manual, Cold Spring Harbor Laboratory, New York, 1989), cDNA molecules were generated from the mRNAs and subsequently isolated, which cDNAs encode the soluble Forms 1 and 2 of the IFNAR protein.

The isolated cDNAs encoding the soluble Form 1 and 2, of the IFNAR protein were introduced, by the above noted standard procedures, into expression vectors with either the early or late SV40 promoters to provide pSVE3 or PSVL constructs, respectively.

The expression of the two soluble forms of IFNAR was demonstrated by transfection of COS-7 cells (monkey kidney cells) with the pSVL constructs. The results of these expression studies revealed that the different structure of the Form 1 and Form 2 proteins profoundly influences the fate of the protein product. Form 1 which has a 7-amino acid terminal tail attached to amino acid 427 of the IFNAR protein and lacks the transmembranal and intracytoplasmic domains, was found to be efficiently secreted into the medium of the COS-7 cell cultures. In contrast, Form 2, which has a deletion of the transmembranal domain, but which conserves almost all of the intracytoplasmic domain was found to be retained within the cell. The results of these expression studies are presented in FIGS. 9a, b.

FIG. 9a shows a reproduction of an immunostained Western blot performed on samples obtained from the culture medium of the COS-7 cells. In this analysis, COS-7 cells transformed by the pSVL vector encoding the Form 1 IFNAR soluble protein, were grown in standard culture medium, and samples were taken of the culture medium which contains the various proteins secreted by the cells. These samples were then separated by standard SDS-PAGE, and the thus separated proteins were then blotted onto a nitrocellulose filter by standard Western blot procedure. The Western blot was then stained using monoclonal antibody, mAb #1 (mAb 64G12, see Example 4). On each SDS-PAGE gel, and hence each Western blot, the following samples were analyzed:

(i) proteins secreted from COS-7 cells transformed with the pSVL vector encoding the Form 1 IFNAR, sample prepared from 12 μl culture medium.;

(ii) proteins secreted from COS-7 cells transformed with only the pSVL vector (i.e. without the Form 1 sequence), which serves as a negative control, sample prepared from 12 μl culture medium, concentrated (×200) before application to gel (sample 'pSVL' in FIG. 9a);

(iii) proteins secreted from COS-7 cells transformed with the pSVL vector encoding the Form 1 IFNAR, sample prepared from 8 μl culture medium, concentrated (×200) before application to gel (sample 'pSVLSαR1' in FIG. 9a);

(iv) proteins secreted from COS-7 cells transformed only with the pSVL vector (i.e. without the Form 1 sequence) which serves as a negative control, sample prepared from 8 μl culture medium, concentrated (×200) before application to gel (sample 'pSVL' in FIG. 9a);

(v) proteins extracted from DAUDI cells, which produce the cell-surface bound IFN receptors and the soluble forms thereof and hence this sample serves as a positive control for mAb #1 immunostaining of the blot and as a molecular weight standard for the IFNARs (sample 'DAUDI' in FIG. 9a); and (vi) radiolabelled molecular weight marker protein were also present in the gel (extreme right hand sample in FIG. 9a).

Thus, from the Western blot of FIG. 9a, it is apparent that the COS-7 cells transformed with the pSVL vector encoding the Form 1 soluble IFNAR protein, can successfully express and secrete this protein, the secreted protein having a molecular weight of about 73 Kd, as expected.

FIG. 9b, shows a reproduction of a Western blot performed on samples obtained from COS-7 cells transformed with pSVL vectors encoding the Form 1 and Form 2 IFNAR proteins. In this analysis, the samples taken from the transformed COS-7 cells were as follows: culture medium samples i.e. containing proteins secreted by the cells; cell membrane samples, i.e. proteins produced by the cells and incorporated into the membranes; cytosol samples i.e. proteins produced by the cells and present in the intracellular compartment (cytosol) of the cells; and nuclei samples, i.e. proteins produced by the cells and associated with the nuclei or nuclear membranes. The preparation of all these samples is described in Example 4 above, and it should be noted that the nuclei sample is obtained from the cell extract samples (from which the membranes and cytosol are separated and isolated) by standard procedures and includes also steps of washing of the nuclei sample with Triton X-100. All the above samples were then separated by standard procedures on SDS-PAGE and Western blotted. The Western blot was then immunostained as above with mAb #1, to yield the blot shown in FIG. 9b, the samples of which are as follows: Lane 1: culture medium from COS-7 cells transformed with only the pSVL vector, without an IFNAR sequence, negative control; Lane 2: culture medium from COS-7 cells transformed with the pSVL vector encoding Form 1 IFNAR; Lane 3: culture medium from COS-7 cells transformed with the pSVL vector encoding Form 2 IFNAR; Lane 4: membranes from COS-7 cells transformed with only the pSVL vector without an IFNAR sequence, negative control; Lane 5: membranes from COS-7 cells transformed with the pSVL vector encoding the Form 2 IFNAR; Lane 6: cytosol from COS-7 cells transformed with only the pSVL vector without an IFNAR sequence, negative control; Lane 7: cytosol from COS-7 cells transformed with the pSVL vector encoding the Form 2 IFNAR; Lane 8: nuclei from COS-7 cells transformed with only the pSVL vector without an IFNAR sequence; and Lane 9: nuclei from COS-7 cells transformed with the pSVL vector encoding the Form 2 IFNAR.

Thus it is apparent from FIG. 9b that the form 1 soluble IFNAR (approx. 73 Kd) is successfully expressed and secreted into the transformed COS-7 cell culture medium, while the Form 2 soluble IFNAR protein is successfully expressed in the COS-7 cells, but is not secreted into the medium, (possibly in the Golgi membranes) and even more so in association with the cell nucleus. The Form 2 soluble IFNAR is larger than the Form 1 soluble IFNAR and shows two components of approx. 80 and 100 Kd. This different localization of the Form 1 and Form 2 cDNA products supports the notion that these cell-produced soluble receptors have distinct functions. For example, as noted in Example 4 above, $U266^R$ cells lacking the transmembranal IFNAR protein can still respond to IFNs by activation of IRF-1 although activation of ISGF3 is lost. Thus, the roles played by the Form 1 and form 2 soluble proteins, including signal transduction, will be further elucidated.

In a further study of the COS-7 cells transformed by (or transfected with) the pSVL vector encoding the Form 1 protein produced in these cells was capable of binding IFN, i.e. the recombinantly produced protein retained its IFN activity. In this study, radioiodinated IFN-α-A was reacted with concentrated medium from COS-7 cells transfected by the cDNA for soluble IFNAR Form 1. After cross-linking, immunoprecipitations were carried out with antibodies to IFN-α and to IFNAR (mAb #2=mAb 21.4, see Example 4). In this analysis, proteins secreted from human $U266^R$ cells, (which cells contain the Form 1 mRNA, lacking the transmembranal IFNAR, see Example 4), were also examined as control samples. The results of this analysis are shown in FIG. 10 which is a reproduction of a SDS-PAGE gel on which were separated the immunoprecipitated, cross-linked samples as noted above. The samples shown in FIG. 10 are as follows: Lane 1: culture medium from COS-7 cells transfected by the pSVL vector encoding the Form 1 soluble IFNAR, immunoprecipitation with anti-IFN-α-2 mAbs and crosslinking with $^{125}$I-IFNα-2; Lane 2: the sample as in Lane 1, but with cross-linking in the presence of unlabelled (cold) IFNα-2 (×50); Lane 3: the sample as in Lane 1, but immunoprecipitation with mAb #2 and cross-linking in the presence of cold IFNα-2 (×50); Lane 4: the sample as in Lane 1, but immunoprecipitation with mAb #2; Lane 5: culture medium from COS-7 cells transfected only by the pSVL vector, without an IFNAR sequence and immunoprecipitation with anti-IFNα-2 mAbs, negative control. Lane 6: the sample as in Lane 5, but immunoprecipitation with mAb #2, negative control; Lane 7: culture medium from $U266^R$ cells, immunoprecipitated with mAb #2 and cross-linking with labelled ($^{125}$I)-IFNα-2 and in the presence of cold IFNα-2; and Lane 8: the sample as in lane 7, but with cross-linking only with the labelled IFNα-2. (Lane 'M' denotes molecular weight standards also run on the gel). Thus, it is apparent from FIG. 10 that binding of IFN to the recombinantly produced Form 1 soluble IFNAR occurs successfully (Lanes 1 and 4). further, the U266$^R$ cells are capable of secreting the Form 1 IFNAR encoded by the corresponding mRNA present in these cells (Lane 8), demonstrating that the soluble receptor does not arise from cleavage of the membranal receptor, at least in these cells, rather it arises from the differentially spliced mRNA (Example 4). Moreover, the mAb #2 is capable of immunoprecipitating the soluble IFNAR protein, although it cannot do so for the membranal receptor extracted by detergents from the cell surface membranes (see Example 4).

Further studies of the ability of the soluble Form 1 IFNAR to bind IFNs, including quantitative studies, have been carried out, preliminarily, by adding the COS-7 cell-secreted product to Daudi cells and measuring the binding of iodinated IFN-α thereto, as has been the preparation of expression vectors encoding the soluble IFNARs for expression thereof in CHO cells (results not shown).

(b) Recombinant production of a soluble IFNAR protein, fusion products, fragments and muteins thereof In part (a) above, the specific preparation of SV-40-derived expression vectors (e.g. sPVL) is described, encoding the soluble Form 1 and Form 2 IFNARs, which vectors when introduced (transfection) into COS-7 host cells result in the successful expression of recombinant Form 1 and Form 2 IFNARs. Using standard recombinant DNA technology, other vectors (and host cells transfected therewith) may be produced for the production of recombinant soluble IFNARs fusion proteins, fragments and muteins thereof, as follows:

An isolated cDNA according to the invention is subjected to site directed mutagenesis with appropriate oligonucleotides so that a termination codon and a polyadenylation site are inserted after the last essential codon of the soluble IFNAR. This construct is then inserted into appropriately constructed expression vectors by techniques well known in the art (Maniatis et al. *Molecular Cloning: A Laboratory Manual*, Cold Spring Harbor Laboratory, New York, 1982). Double-stranded cDNA is linked to plasmid vectors by homopolymeric tailing or by restriction linking involving the use of synthetic DNA linkers or blunt-ended ligation techniques. DNA ligases are used to ligate the DNA molecules and undesirable joining is avoided by treatment of DNA strands with alkaline phosphatase.

The production of a fused protein comprising a soluble IFNAR and, e.g., the constant region of IgG$_1$ heavy chain may be carried out as follows: the DNA of a soluble IFNAR is subjected to site-directed mutagenesis with appropriate oligonucleotides so that a unique restriction site is introduced immediately after the coding sequence. A plasmid bearing the constant region of IgG$_1$ heavy chain, e.g. pRKCO4$_2$Fc$_1$ (Byrn R. A. et al., 1990, Nature, 344:667–670) is subjected to similar site-directed mutagenesis to introduce the same unique restriction site as close as possible to Asp 216 of IgG$_1$ heavy chain in a way that allows translation in phase of the fused protein. A dsDNA fragment consisting of 5' untranslated sequences and encoding for a soluble IFNAR is prepared by digestion at the unique restriction sites. The mutated pRKCD4$_2$Fc$_1$ is similarly digested to generate a large fragment containing the plasmid and the IgG$_1$ sequences. The two fragments are then ligated to generate a new plasmid encoding a polypeptide precursor consisting of the N-terminal soluble IFNAR and about 227 C-terminal amino acids of IgG$_1$ heavy chain (hinge region and CH2 and CH3 domains). The DNA encoding the fused protein may be isolated from the plasmid by digestion with appropriate restriction enzymes and then inserted into an efficient expression vector.

In order to be capable of expressing a soluble IFNAR, its muteins or the fused proteins, an expression vector should comprise also specific nucleotide sequences containing transcriptional and translational regulatory information linked to the DNA coding for the desired protein in such a way as to permit gene expression and production of the protein. First, in order for the gene to be transcribed, it must be preceded by a promoter recognizable by RNA polymerase, to which the polymerase binds and thus initiates the transcription process. There are a variety of such promoters in use, which work with different efficiencies (strong and weak promoters). They are different for prokaryotic and eukaryotic cells.

The promoters that can be used in the present invention may be either constitutive, for example, the int promoter of bacteriophage lambda, the bla promoter of the β-lactamase gene of pBR322, and the CAT promoter of the chloramphenicol acetyl transferase gene of pPR325, etc., or inducible, such as the prokaryotic promoters including the major right and left promoters of bacteriophage lambda (P$_L$ and P$_R$), the trp, recA, lacZ, lacI, ompF and gal promoters of *E. coli*, or the trp-lac hybrid promoter, etc. (Glick, B. R. (1987) J. Ind. Microbiol. 1:277–282). Besides the use of strong promoters to generate large quantities of mRNA, in order to achieve high levels of gene expression in prokaryotic cells, it is necessary to use also ribosome-binding sites to ensure that the mRNA is efficiently translated. One example is the Shine-Dalgarno sequence (SD sequence) appropriately positioned from the initiation codon and complementary to the 3'-terminal sequence of 16S RNA.

For eukaryotic hosts, different transcriptional and translational regulatory sequences may be employed, depending on the nature of the host. They may be derived from viral sources, such as adenovirus, bovine papilloma virus, Simian virus, or the like, where the regulatory signals are associated with a particular gene which has a high level of expression. Examples are the TK promoter of Herpes virus, the SV40 early promoter, the yeast gal4 gene promoter, etc. Transcriptional initiation regulator signals may be selected which allow for repression and activation, so that expression of the genes can be modulated.

The DNA molecule comprising the nucleotide sequence coding for a soluble IFNAR of the invention or its fragments or muteins or fused proteins thereof, and the operably linked transcriptional and translational regulatory signals is inserted into a vector which is capable of integrating the desired gene sequences into the host cell chromosome. In order to be able to select the cells which have stably integrated the introduced DNA into their chromosomes, one or more markers which allow for selection of host cells which contain the expression vector is used. The marker may provide for prototrophy to an auxotropic host, biocide resistance, e.g., antibiotics, or heavy metals, such as copper, or the like. The selectable marker gene can either be directly linked to the DNA gene sequences to be expressed, or introduced into the same cell by cotransfection. Additional elements may also be needed for optimal synthesis of single chain binding protein mRNA. These elements may include splice signals, as well as transcription promoters, enhancers, and termination signals. cDNA expression vectors incorporating such elements include those described by Okayama, H., (1983) Mol. Cel. Biol. 3:280.

In a preferred embodiment, the introduced DNA molecule will be incorporated into a plasmid or viral vector capable of autonomous replication in the recipient host. Factors of importance in selecting a particular plasmid or vital vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Preferred prokaryotic vectors include plasmids such as those capable of replication in E. coli, for example, pBR322, ColE1, pSC101, pACYC 184, etc. (see Maniatis et al., op.cit.); Bacillus plasmids such as pC194, pC221, pT127, etc. (Gryczan, T., "The Molecular Biology of the Bacilli", Academic Press, New York (1982), pp. 307–329); Streptomyces plasmids including pIJ101 (Kendall, K. J. et al. (1987) J. Bacteriol. 169:4177–4183); Streptomyces bacteriophages such as φC31 (Chater, K.F. et al., in "Sixth International Symposium on Actinomycetales Biology", Akademiai Kaido, Budapest, Hungary (1986), pp. 45–54), and Pseudomonas plasmids (John, J. F., et al. (1986) Rev. Infect. Dis. 8:693–704), and Izaki, K. (1978) Jpn. J. Bacteriol. 33:729–742).

Preferred eukaryotic plasmids include BPV, vaccinia, SV40, 2-micron circle, etc., or their derivatives. Suck plasmids are well known in the art (Botstein, D., et al. (1982) Miami Wint. Symp. 19:265–274; Broach, J. R., in "The Molecular Biology of the Yeast Saccharomyces: Life Cycle and Inheritance", Cold Spring Harbor Laboratory, Cold Spring Harbor, N.Y., pp. 445–470 (1981); Broach, J. R., (1982) Cell 28:203–204; Bollon, D. P., et al. 1980) J. Clin. Hematol. Oncol. 10:39–48; Maniatis, T., in "Cell Biology: A Comprehensive Treatise, Vol. 3: Gene Expression", Academic Press, New York, pp. 563–608 (1980)).

Once the vector or DNA sequence containing the construct(s) has been prepared for expression, the expression vector may be introduced into an appropriate host cell by any of a variety of suitable means, such as transformation, transfection, lipofection, conjugation, protoplast fusion, electroporation, calcium phosphate precipitation, direct microinjection, etc.

Host cells to be used in this invention may be either prokaryotic or eukaryotic. Preferred prokaryotic hosts include bacteria such as E. coli, Bacillus, Streptomyces, Pseudomonas, Salmonella, Serratia, etc. The most preferred prokaryotic host is E. coli. Bacterial hosts of particular interest include E. coli K12 strain 294 (ATCC 31446), E. coli X1776 (ATCC 31537), E. coli W3110 (F, lambda, prototropic (ATCC 27325)), and other enterobacterium such as Salmonella typhimurium or Serratia narcescens and various Pseudomonas species. Under such conditions, the protein will not be glycosylated. The prokaryotic host must be compatible with the replicon and control sequences in the expression plasmid.

Preferred eukaryotic hosts are mammalian cells, e.g., human, monkey, mouse and chinese hamster ovary (CHO) cells, because they provide post-translational modifications to protein molecules including correct folding, correct disulfide bond formation as well as glycosylation at correct sites. Also yeast cells and insect cells can carry out post-translational peptide modifications including high mannose glycosylation. A number of recombinant DNA strategies exist which utilize strong promoter sequences and high copy number of plasmids which can be utilized for production of the desired proteins in yeast and in insect cells. Yeast cells recognize leader sequences on cloned mammalian gene products and secrete peptides bearing leader sequences.

After the introduction of the vector, the host cells are grown in a selective medium, which selects for the growth of vector-containing cells. Expression of the cloned gene sequence(s) results in the production of the soluble IFNAR, a fusion protein, or a mutein or a fragment thereof. The expressed protein is then isolated and purified by any conventional procedure involving extraction, precipitation, chromatography, electrophoresis, or the like, or by affinity chromatography, using anti-soluble IFNAR monoclonal antibodies immobilized on a gel matrix contained within a column. Crude preparations containing the soluble IFNAR are passed through the column whereby the soluble IFNAR will be bound to the column by the specific antibody while the impurities will pass through. After washing, the protein is eluted from the gel at a high or a low pH, eg. pH 11 or pH 2.

We claim:

1. An isolated DNA encoding a polypeptide having SEQ ID NO:11 or SEQ ID NO:12.

2. A recombinant expression vector comprising a DNA sequence according to claim 1.

3. A process for preparing a mammalian, soluble, non-membrane bound form of an IFNAR, comprising culturing a suitable host cell comprising a vector according to claim 2 under conditions promoting expression.

4. An isolated DNA in accordance with claim 1, which is a cDNA.

5. A recombinant expression vector comprising a DNA sequence according to claim 4.

6. A process for preparing a mammalian, soluble, non-membrane bound form of an IFNAR, comprising culturing a suitable host cell comprising a vector according to claim 5 under conditions promoting expression.

7. An isolated DNA in accordance with claim 1, wherein said polypeptide has SEQ ID NO:11.

8. A recombinant expression vector comprising a DNA sequence according to claim 7.

9. A process for preparing a mammalian, soluble, non-membrane bound form of an IFNAR, comprising culturing a suitable host cell comprising a vector according to claim 8 under conditions promoting expression.

10. An isolated DNA in accordance with claim 1, wherein said polypeptide has SEQ ID NO:12.

11. A recombinant expression vector comprising a DNA sequence according to claim 10.

12. A process for preparing a mammalian, soluble, non-membrane bound form of an IFNAR, comprising culturing a suitable host cell comprising a vector according to claim 11 under conditions promoting expression.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 360 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

```
AATTTGAAAC  CACTGACTGT  ATATTGTGTG  AAAGCCAGAG  CACACACCAT  GGATGAAAAG      60

CTGAATAAAA  GCAGTGTTTT  TAGTGACGCT  GTATGTGAGA  AAACAAAACC  AGGAAATACC     120

TCTAAAATTT  GGCTTATAGT  TGGAATTTGT  ATTGCATTAT  TTGCTCTCCC  GTTTGTCATT     180

TATGCTGCGA  AAGTCTTCTT  GAGATGCATC  AATTATGTCT  TCTTTCCATC  ACTTAAACCT     240

TCTTCCAGTA  TAGATGAGTA  TTTCTCTGAA  CAGCCATTGA  AGAATCTTCT  GCTTTCAACT     300
```

```
TCTGAGGAAC  AAATCGAAAA  ATGTTTCATA  ATTGAAAATA  TAAGCACAAT  TGCTACAGTA        360
```

( 2 ) INFORMATION FOR SEQ ID NO:2:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

```
ACGTGAATTC  GCAGTGTTTT  TA                                                     22
```

( 2 ) INFORMATION FOR SEQ ID NO:3:

( i ) SEQUENCE CHARACTERISTICS:
        ( A ) LENGTH: 133 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

```
GCAGTGTTTT  TAGTGACGCT  GTATGTGAGA  ATATTTCTCT  GAACAGCCAT  TGAAGAATCT         60
TCTGCTTTCA  ACTTCTGAGG  AACAAATCGA  AAAATGTTTC  ATAATTGAAA  ATATAAGCAC        120
AATTGCTACA  GTA                                                               133
```

( 2 ) INFORMATION FOR SEQ ID NO:4:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
Cys  Glu  Lys  Thr  Lys  Pro  Gly
 1                 5
```

( 2 ) INFORMATION FOR SEQ ID NO:5:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

```
Asp  Glu  Tyr  Phe  Ser  Glu  Gln  Pro  Leu  Lys
 1                 5                          10
```

( 2 ) INFORMATION FOR SEQ ID NO:6:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

Cys Glu Asn Ile Ser Leu Asn Ser His
1               5

( 2 ) INFORMATION FOR SEQ ID NO:7:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

GCTCGAATTC CACTGACTGT ATATTGTGTG                             30

( 2 ) INFORMATION FOR SEQ ID NO:8:

( i ) SEQUENCE CHARACTERISTICS:
        ( A ) LENGTH: 168 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..168

( x i ) SEQUENCE DESCRIPTION: SEQ ID NO:8:

CCA CTG ACT GTA TAT TGT GTG AAA GCC AGA GCA CAC ACC ATG GAT GAA    48
Pro Leu Thr Val Tyr Cys Val Lys Ala Arg Ala His Thr Met Asp Glu
1               5                   10                  15

AGT GAC GCT GTA TGT GAG TAT TTC TCT GAA CAG CCA TTG AAG AAT CTT    96
Ser Asp Ala Val Cys Glu Tyr Phe Ser Glu Gln Pro Leu Lys Asn Leu
                20                  25                  30

CTG CTT TCA ACT TCT GAG GAA CAA ATC GAA AAA TGT TTC ATA ATT GAA   144
Leu Leu Ser Thr Ser Glu Glu Gln Ile Glu Lys Cys Phe Ile Ile Glu
            35                  40                  45

AAT ATA AGC ACA ATT GCT ACA GTA                                   168
Asn Ile Ser Thr Ile Ala Thr Val
        50                  55

( 2 ) INFORMATION FOR SEQ ID NO:9:

( i ) SEQUENCE CHARACTERISTICS:
        ( A ) LENGTH: 56 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:9:

Pro Leu Thr Val Tyr Cys Val Lys Ala Arg Ala His Thr Met Asp Glu
1               5                   10                  15

Ser Asp Ala Val Cys Glu Tyr Phe Ser Glu Gln Pro Leu Lys Asn Leu
                20                  25                  30

Leu Leu Ser Thr Ser Glu Glu Gln Ile Glu Lys Cys Phe Ile Ile Glu
            35                  40                  45

Asn Ile Ser Thr Ile Ala Thr Val
        50                  55

( 2 ) INFORMATION FOR SEQ ID NO:10:

( i ) SEQUENCE CHARACTERISTICS:
  ( A ) LENGTH: 557 amino acids
  ( B ) TYPE: amino acid
  ( C ) STRANDEDNESS: single
  ( D ) TOPOLOGY: linear ( i i ) MOLECULE TYPE: protein ( x i ) SEQUENCE DESCRIPTION: SEQ ID NO:10:

| Met | Met | Val | Val | Leu | Leu | Gly | Ala | Thr | Thr | Leu | Val | Leu | Val | Ala | Val |
|---|---|---|---|---|---|---|---|---|---|---|---|---|---|---|---|
| 1 | | | | 5 | | | | | 10 | | | | | 15 | |
| Gly | Pro | Trp | Val | Leu | Ser | Ala | Ala | Ala | Gly | Gly | Lys | Asn | Leu | Lys | Ser |
| | | | 20 | | | | | 25 | | | | | 30 | | |
| Pro | Gln | Lys | Val | Glu | Val | Asp | Ile | Ile | Asp | Asp | Asn | Phe | Ile | Leu | Arg |
| | | 35 | | | | | 40 | | | | | 45 | | | |
| Trp | Asn | Arg | Ser | Asp | Glu | Ser | Val | Gly | Asn | Val | Thr | Phe | Ser | Phe | Asp |
| | 50 | | | | | 55 | | | | | 60 | | | | |
| Tyr | Gln | Lys | Thr | Gly | Met | Asp | Asn | Trp | Ile | Lys | Leu | Ser | Gly | Cys | Gln |
| 65 | | | | | 70 | | | | | 75 | | | | | 80 |
| Asn | Ile | Thr | Ser | Thr | Lys | Cys | Asn | Phe | Ser | Ser | Leu | Lys | Leu | Asn | Val |
| | | | | 85 | | | | | 90 | | | | | 95 | |
| Tyr | Glu | Glu | Ile | Lys | Leu | Arg | Ile | Arg | Ala | Glu | Lys | Glu | Asn | Thr | Ser |
| | | | 100 | | | | | 105 | | | | | 110 | | |
| Ser | Trp | Tyr | Glu | Val | Asp | Ser | Phe | Thr | Pro | Phe | Arg | Lys | Ala | Gln | Ile |
| | | 115 | | | | | 120 | | | | | 125 | | | |
| Gly | Pro | Pro | Glu | Val | His | Leu | Glu | Ala | Glu | Asp | Lys | Ala | Ile | Val | Ile |
| | 130 | | | | | 135 | | | | | 140 | | | | |
| His | Ile | Ser | Pro | Gly | Thr | Lys | Asp | Ser | Val | Met | Trp | Ala | Leu | Asp | Gly |
| 145 | | | | | 150 | | | | | 155 | | | | | 160 |
| Leu | Ser | Phe | Thr | Tyr | Ser | Leu | Leu | Ile | Trp | Lys | Asn | Ser | Ser | Gly | Val |
| | | | | 165 | | | | | 170 | | | | | 175 | |
| Glu | Glu | Arg | Ile | Glu | Asn | Ile | Tyr | Ser | Arg | His | Lys | Ile | Tyr | Lys | Leu |
| | | | 180 | | | | | 185 | | | | | 190 | | |
| Ser | Pro | Glu | Thr | Thr | Tyr | Cys | Leu | Lys | Val | Lys | Ala | Ala | Leu | Leu | Thr |
| | | 195 | | | | | 200 | | | | | 205 | | | |
| Ser | Trp | Lys | Ile | Gly | Val | Tyr | Ser | Pro | Val | His | Cys | Ile | Lys | Thr | Thr |
| | 210 | | | | | 215 | | | | | 220 | | | | |
| Val | Glu | Asn | Glu | Leu | Pro | Pro | Pro | Glu | Asn | Ile | Glu | Val | Ser | Val | Gln |
| 225 | | | | | 230 | | | | | 235 | | | | | 240 |
| Asn | Gln | Asn | Tyr | Val | Leu | Lys | Trp | Asp | Tyr | Thr | Tyr | Ala | Asn | Met | Thr |
| | | | | 245 | | | | | 250 | | | | | 255 | |
| Phe | Gln | Val | Gln | Trp | Leu | His | Ala | Phe | Leu | Lys | Arg | Asn | Pro | Gly | Asn |
| | | | 260 | | | | | 265 | | | | | 270 | | |
| His | Leu | Tyr | Lys | Trp | Lys | Gln | Ile | Pro | Asp | Cys | Glu | Asn | Val | Lys | Thr |
| | | 275 | | | | | 280 | | | | | 285 | | | |
| Thr | Gln | Cys | Val | Phe | Pro | Gln | Asn | Val | Phe | Gln | Lys | Gly | Ile | Tyr | Leu |
| | 290 | | | | | 295 | | | | | 300 | | | | |
| Leu | Arg | Val | Gln | Ala | Ser | Asp | Gly | Asn | Asn | Thr | Ser | Phe | Trp | Ser | Glu |
| 305 | | | | | 310 | | | | | 315 | | | | | 320 |
| Glu | Ile | Lys | Phe | Asp | Thr | Glu | Ile | Gln | Ala | Phe | Leu | Leu | Pro | Pro | Val |
| | | | | 325 | | | | | 330 | | | | | 335 | |
| Phe | Asn | Ile | Arg | Ser | Leu | Ser | Asp | Ser | Phe | His | Ile | Tyr | Ile | Gly | Ala |
| | | | 340 | | | | | 345 | | | | | 350 | | |
| Pro | Lys | Gln | Ser | Gly | Asn | Thr | Pro | Val | Ile | Gln | Asp | Tyr | Pro | Leu | Ile |
| | | 355 | | | | | 360 | | | | | 365 | | | |

| | | | | | | | | | | | | | | | |
|---|---|---|---|---|---|---|---|---|---|---|---|---|---|---|---|
|Tyr|Glu 370|Ile|Ile|Phe|Trp|Glu 375|Asn|Thr|Ser|Asn|Ala 380|Glu|Arg|Lys|Ile|
|Ile 385|Glu|Lys|Lys|Thr|Asp 390|Val|Thr|Val|Pro|Asn 395|Leu|Lys|Pro|Leu|Thr 400|
|Val|Tyr|Cys|Val|Lys 405|Ala|Arg|Ala|His|Thr 410|Met|Asp|Glu|Lys|Leu 415|Asn|
|Lys|Ser|Ser|Val 420|Phe|Ser|Asp|Ala|Val 425|Cys|Glu|Lys|Thr|Lys 430|Pro|Gly|
|Asn|Thr|Ser 435|Lys|Ile|Trp|Leu|Ile 440|Val|Gly|Ile|Cys|Ile 445|Ala|Leu|Phe|
|Ala|Leu 450|Pro|Phe|Val|Ile|Tyr 455|Ala|Ala|Lys|Val|Phe 460|Leu|Arg|Cys|Ile|
|Asn 465|Tyr|Val|Phe|Phe|Pro 470|Ser|Leu|Lys|Pro|Ser 475|Ser|Ser|Ile|Asp|Glu 480|
|Tyr|Phe|Ser|Glu|Gln 485|Pro|Leu|Lys|Asn|Leu 490|Leu|Leu|Ser|Thr|Ser 495|Glu|
|Glu|Gln|Ile|Glu 500|Lys|Cys|Phe|Ile|Ile 505|Glu|Asn|Ile|Ser|Thr 510|Leu|Ala|
|Thr|Val|Glu 515|Glu|Thr|Asn|Gln|Thr 520|Asp|Glu|Asp|His|Lys 525|Lys|Tyr|Ser|
|Ser|Gln 530|Thr|Ser|Gln|Asp|Ser 535|Gly|Asn|Tyr|Ser|Asn 540|Glu|Asp|Glu|Ser|
|Glu 545|Ser|Lys|Thr|Ser|Glu 550|Glu|Leu|Gln|Gln|Asp 555|Phe|Val| | | |

( 2 ) INFORMATION FOR SEQ ID NO:11:

( i ) SEQUENCE CHARACTERISTICS:
( A ) LENGTH: 434 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:11:

| | | | | | | | | | | | | | | | |
|---|---|---|---|---|---|---|---|---|---|---|---|---|---|---|---|
|Met 1|Met|Val|Val|Leu 5|Leu|Gly|Ala|Thr|Thr 10|Leu|Val|Leu|Val|Ala 15|Val|
|Gly|Pro|Trp|Val 20|Leu|Ser|Ala|Ala|Ala 25|Gly|Gly|Lys|Asn|Leu 30|Lys|Ser|
|Pro|Gln|Lys 35|Val|Glu|Val|Asp|Ile 40|Ile|Asp|Asp|Asn|Phe 45|Ile|Leu|Arg|
|Trp|Asn 50|Arg|Ser|Asp|Glu|Ser 55|Val|Gly|Asn|Val|Thr 60|Phe|Ser|Phe|Asp|
|Tyr 65|Gln|Lys|Thr|Gly|Met 70|Asp|Asn|Trp|Ile|Lys 75|Leu|Ser|Gly|Cys|Gln 80|
|Asn|Ile|Thr|Ser|Thr 85|Lys|Cys|Asn|Phe|Ser 90|Ser|Leu|Lys|Leu|Asn 95|Val|
|Tyr|Glu|Glu|Ile 100|Lys|Leu|Arg|Ile|Arg 105|Ala|Glu|Lys|Glu|Asn 110|Thr|Ser|
|Ser|Trp|Tyr 115|Glu|Val|Asp|Ser|Phe 120|Thr|Pro|Phe|Arg|Lys 125|Ala|Gln|Ile|
|Gly|Pro|Pro 130|Glu|Val|His|Leu 135|Glu|Ala|Glu|Asp|Lys 140|Ala|Ile|Val|Ile|
|His 145|Ile|Ser|Pro|Gly|Thr 150|Lys|Asp|Ser|Val|Met 155|Trp|Ala|Leu|Asp|Gly 160|

```
Leu  Ser  Phe  Thr  Tyr  Ser  Leu  Leu  Ile  Trp  Lys  Asn  Ser  Ser  Gly  Val
               165                 170                      175

Glu  Glu  Arg  Ile  Glu  Asn  Ile  Tyr  Ser  Arg  His  Lys  Ile  Tyr  Lys  Leu
               180                 185                      190

Ser  Pro  Glu  Thr  Thr  Tyr  Cys  Leu  Lys  Val  Lys  Ala  Ala  Leu  Leu  Thr
               195                 200                      205

Ser  Trp  Lys  Ile  Gly  Val  Tyr  Ser  Pro  Val  His  Cys  Ile  Lys  Thr  Thr
               210                 215                      220

Val  Glu  Asn  Glu  Leu  Pro  Pro  Glu  Asn  Ile  Glu  Val  Ser  Val  Gln
225                      230                 235                      240

Asn  Gln  Asn  Tyr  Val  Leu  Lys  Trp  Asp  Tyr  Thr  Tyr  Ala  Asn  Met  Thr
               245                 250                      255

Phe  Gln  Val  Gln  Trp  Leu  His  Ala  Phe  Leu  Lys  Arg  Asn  Pro  Gly  Asn
               260                 265                      270

His  Leu  Tyr  Lys  Trp  Lys  Gln  Ile  Pro  Asp  Cys  Glu  Asn  Val  Lys  Thr
               275                 280                      285

Thr  Gln  Cys  Val  Phe  Pro  Gln  Asn  Val  Phe  Gln  Lys  Gly  Ile  Tyr  Leu
               290                 295                      300

Leu  Arg  Val  Gln  Ala  Ser  Asp  Gly  Asn  Asn  Thr  Ser  Phe  Trp  Ser  Glu
305                      310                 315                      320

Glu  Ile  Lys  Phe  Asp  Thr  Glu  Ile  Gln  Ala  Phe  Leu  Leu  Pro  Pro  Val
               325                 330                      335

Phe  Asn  Ile  Arg  Ser  Leu  Ser  Asp  Ser  Phe  His  Ile  Tyr  Ile  Gly  Ala
               340                 345                      350

Pro  Lys  Gln  Ser  Gly  Asn  Thr  Pro  Val  Ile  Gln  Asp  Tyr  Pro  Leu  Ile
               355                 360                      365

Tyr  Glu  Ile  Ile  Phe  Trp  Glu  Asn  Thr  Ser  Asn  Ala  Glu  Arg  Lys  Ile
               370                 375                      380

Ile  Glu  Lys  Lys  Thr  Asp  Val  Thr  Val  Pro  Asn  Leu  Lys  Pro  Leu  Thr
385                      390                 395                      400

Val  Tyr  Cys  Val  Lys  Ala  Arg  Ala  His  Thr  Met  Asp  Glu  Lys  Leu  Asn
               405                 410                      415

Lys  Ser  Ser  Val  Phe  Ser  Asp  Ala  Val  Cys  Glu  Asn  Ile  Ser  Leu  Asn
               420                 425                      430

Ser  His
```

( 2 ) INFORMATION FOR SEQ ID NO:12:

( i ) SEQUENCE CHARACTERISTICS:
        ( A ) LENGTH: 496 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:12:

```
Met  Met  Val  Val  Leu  Leu  Gly  Ala  Thr  Thr  Leu  Val  Leu  Val  Ala  Val
1                   5                   10                      15

Gly  Pro  Trp  Val  Leu  Ser  Ala  Ala  Gly  Gly  Lys  Asn  Leu  Lys  Ser
               20                  25                      30

Pro  Gln  Lys  Val  Glu  Val  Asp  Ile  Ile  Asp  Asp  Asn  Phe  Ile  Leu  Arg
               35                  40                      45

Trp  Asn  Arg  Ser  Asp  Glu  Ser  Val  Gly  Asn  Val  Thr  Phe  Ser  Phe  Asp
          50                  55                      60

Tyr  Gln  Lys  Thr  Gly  Met  Asp  Asn  Trp  Ile  Lys  Leu  Ser  Gly  Cys  Gln
65                  70                  75                      80
```

-continued

```
Asn  Ile  Thr  Ser  Thr  Lys  Cys  Asn  Phe  Ser  Ser  Leu  Lys  Leu  Asn  Val
               85                      90                           95

Tyr  Glu  Glu  Ile  Lys  Leu  Arg  Ile  Arg  Ala  Glu  Lys  Glu  Asn  Thr  Ser
              100                     105                          110

Ser  Trp  Tyr  Glu  Val  Asp  Ser  Phe  Thr  Pro  Phe  Arg  Lys  Ala  Gln  Ile
              115                     120                          125

Gly  Pro  Pro  Glu  Val  His  Leu  Glu  Ala  Glu  Asp  Lys  Ala  Ile  Val  Ile
     130                          135                     140

His  Ile  Ser  Pro  Gly  Thr  Lys  Asp  Ser  Val  Met  Trp  Ala  Leu  Asp  Gly
145                          150                     155                     160

Leu  Ser  Phe  Thr  Tyr  Ser  Leu  Leu  Ile  Trp  Lys  Asn  Ser  Ser  Gly  Val
               165                     170                          175

Glu  Glu  Arg  Ile  Glu  Asn  Ile  Tyr  Ser  Arg  His  Lys  Ile  Tyr  Lys  Leu
              180                     185                          190

Ser  Pro  Glu  Thr  Thr  Tyr  Cys  Leu  Lys  Val  Lys  Ala  Ala  Leu  Leu  Thr
          195                     200                     205

Ser  Trp  Lys  Ile  Gly  Val  Tyr  Ser  Pro  Val  His  Cys  Ile  Lys  Thr  Thr
     210                          215                     220

Val  Glu  Asn  Glu  Leu  Pro  Pro  Glu  Asn  Ile  Glu  Val  Ser  Val  Gln
225                      230                     235                     240

Asn  Gln  Asn  Tyr  Val  Leu  Lys  Trp  Asp  Tyr  Thr  Tyr  Ala  Asn  Met  Thr
               245                     250                          255

Phe  Gln  Val  Gln  Trp  Leu  His  Ala  Phe  Leu  Lys  Arg  Asn  Pro  Gly  Asn
               260                     265                          270

His  Leu  Tyr  Lys  Trp  Lys  Gln  Ile  Pro  Asp  Cys  Glu  Asn  Val  Lys  Thr
          275                     280                     285

Thr  Gln  Cys  Val  Phe  Pro  Gln  Asn  Val  Phe  Gln  Lys  Gly  Ile  Tyr  Leu
     290                          295                     300

Leu  Arg  Val  Gln  Ala  Ser  Asp  Gly  Asn  Asn  Thr  Ser  Phe  Trp  Ser  Glu
305                      310                     315                     320

Glu  Ile  Lys  Phe  Asp  Thr  Glu  Ile  Gln  Ala  Phe  Leu  Leu  Pro  Pro  Val
               325                     330                          335

Phe  Asn  Ile  Arg  Ser  Leu  Ser  Asp  Ser  Phe  His  Ile  Tyr  Ile  Gly  Ala
               340                     345                          350

Pro  Lys  Gln  Ser  Gly  Asn  Thr  Pro  Val  Ile  Gln  Asp  Tyr  Pro  Leu  Ile
          355                     360                     365

Tyr  Glu  Ile  Ile  Phe  Trp  Glu  Asn  Thr  Ser  Asn  Ala  Glu  Arg  Lys  Ile
     370                     375                     380

Ile  Glu  Lys  Lys  Thr  Asp  Val  Thr  Val  Pro  Asn  Leu  Lys  Pro  Leu  Thr
385                     390                     395                          400

Val  Tyr  Cys  Val  Lys  Ala  Arg  Ala  His  Thr  Met  Asp  Glu  Ser  Asp  Ala
               405                     410                          415

Val  Cys  Glu  Tyr  Phe  Ser  Glu  Gln  Pro  Leu  Lys  Asn  Leu  Leu  Leu  Ser
               420                     425                          430

Thr  Ser  Glu  Glu  Gln  Ile  Glu  Lys  Cys  Phe  Ile  Ile  Glu  Asn  Ile  Ser
          435                     440                     445

Thr  Ile  Ala  Thr  Val  Glu  Glu  Thr  Asn  Gln  Thr  Asp  Glu  Asp  His  Lys
     450                     455                     460

Lys  Tyr  Ser  Ser  Gln  Thr  Ser  Gln  Asp  Ser  Gly  Asn  Tyr  Ser  Asn  Glu
465                     470                     475                          480

Asp  Glu  Ser  Glu  Ser  Lys  Thr  Ser  Glu  Glu  Leu  Gln  Gln  Asp  Phe  Val
               485                     490                          495
```